(12) United States Patent
Pike et al.

(10) Patent No.: US 6,186,141 B1
(45) Date of Patent: Feb. 13, 2001

(54) UNIT DOSE DISPENSING DEVICE

(75) Inventors: Gregory Charles Pike, St Kilda East; Ingo Helmuth Riedel, Monbulk; Stephan Smith, St Kilda, all of (AU)

(73) Assignee: Glaxo Wellcome Inc., Research Triangle Park, NC (US)

(*) Notice: Under 35 U.S.C. 154(b), the term of this patent shall be extended for 0 days.

(21) Appl. No.: 09/180,277

(22) PCT Filed: May 9, 1997

(86) PCT No.: PCT/AU97/00283

§ 371 Date: Jan. 29, 1999

§ 102(e) Date: Jan. 29, 1999

(87) PCT Pub. No.: WO97/42992

PCT Pub. Date: Nov. 20, 1997

(30) Foreign Application Priority Data

May 10, 1996 (AU) .................................................. PN 9764

(51) Int. Cl.[7] .................................................. A61M 15/00
(52) U.S. Cl. ........................... 128/203.12; 128/203.21
(58) Field of Search ...................... 128/200.14, 200.18, 128/200.22, 200.23, 203.12, 203.21, 205.21; 239/3, 690, 692, 704, 706, 33, 338

(56) References Cited

U.S. PATENT DOCUMENTS

| | | | |
|---|---|---|---|
| 3,888,253 | * | 6/1975 | Watt et al. ............................ 128/266 |
| 3,906,950 | * | 9/1975 | Cocozza ............................... 128/266 |
| 3,949,751 | * | 4/1976 | Birch et al. ........................... 128/266 |
| 3,971,377 | * | 7/1976 | Damani ................................ 128/266 |
| 4,884,565 | * | 12/1989 | Cocozza ........................... 128/203.21 |
| 4,995,385 | * | 2/1991 | Valentini et al. ................ 128/203.21 |
| 5,372,128 | * | 12/1994 | Haber et al. ..................... 128/203.21 |
| 5,471,541 | | 11/1995 | Ritsky et al. . |
| 5,601,077 | | 2/1997 | Imbert . |

FOREIGN PATENT DOCUMENTS

| | | |
|---|---|---|
| 679443 | 11/1995 | (EP) . |
| 711571 | 5/1996 | (EP) . |
| WO 96/04947 | 2/1996 | (WO) . |
| WO 96/12513 | 5/1996 | (WO) . |
| WO 96/24440 | 8/1996 | (WO) . |
| WO 96/25190 | 8/1996 | (WO) . |
| WO 96/29109 | 9/1996 | (WO) . |
| WO 97/02062 | 1/1997 | (WO) . |
| WO 97/06842 | 2/1997 | (WO) . |

* cited by examiner

*Primary Examiner*—John G. Weiss
*Assistant Examiner*—Teena Mitchell
(74) *Attorney, Agent, or Firm*—Bacon & Thomas

(57) ABSTRACT

A device for dispensing a unit dose of substance comprises a nozzle assembly (2) including a container (24) housing a unit dose of the substance, and an outer body (4) to which the nozzle assembly (2) is releasably attached. The body (4) includes a system actuable to effect discharge of the substance from the nozzle assembly (2) and actuating means operably by a user to effect discharge. Preferably the discharge system comprises a spring-loaded air piston (68) actuable to inject air into the container (24) to cause discharge of the substance. In one embodiment a driving spring for the air piston is loaded with spring energy by the action of installing the nozzle assembly on the body, the driving spring thereafter being held in a cocked state until operating of the actuating means by the user to effect release of the spring energy to cause discharge.

23 Claims, 18 Drawing Sheets

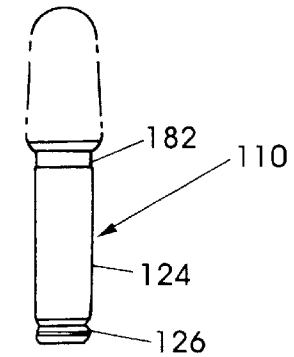
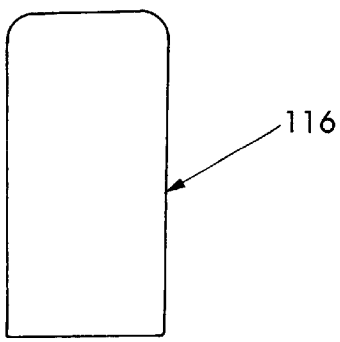
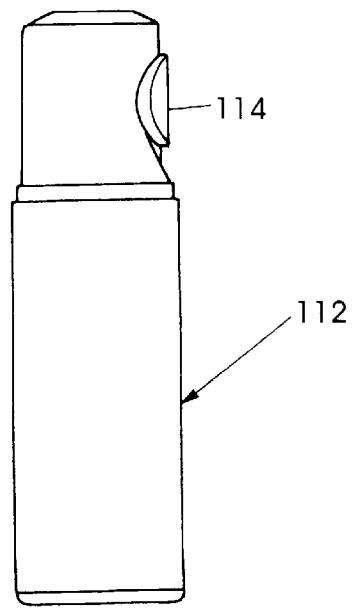
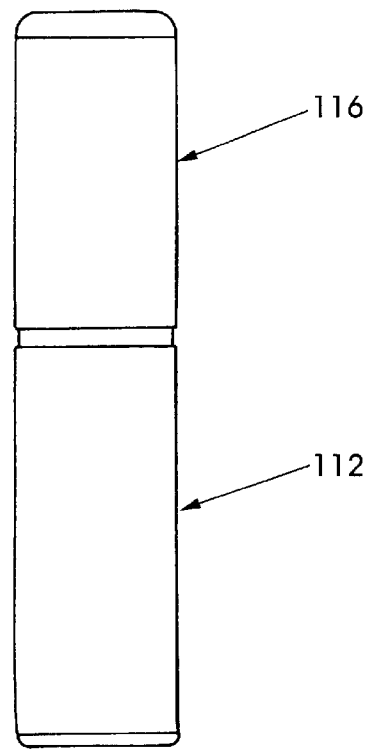
FIG. 8  FIG. 9  FIG. 10

1

UNIT DOSE DISPENSING DEVICE

The present invention relates to a device for dispensing a unit dose of a substance, such as a pharmaceutical, medicinal, or therapeutic substance. More particularly the invention relates to a device for dispensing a unit dose of such a substance into a body cavity. A particularly preferred form of the invention is intended for intranasal administration.

In International Patent Application PCT/EP94/01859 (W094/28956) there is disclosed a device for administration of a pharmaceutical substance from a capsule containing the substance. The capsule is compressed with a pressure sufficient to burst the capsule and to expel the contents in spray form through a discharge outlet. While this previously proposed device does operate satisfactorily the device is relatively bulky and hence not easy to carry on the person, for example in a shirt or jacket pocket. In addition the device is adapted to be reloaded after use with a fresh capsule of substance, but due to the nature of the mechanism within the device, some difficulties may be encountered with the reloading procedure.

There have been proposed unit dose dispensers in which a pharmaceutical substance sealed within an internal chamber of the device is expelled by operation of a piston actuated manually by the user. These previously proposed devices are intended for one use only and when the unit dose has been expelled the entire device must be discarded. Due to the relatively high cost of the overall device which must be discarded after each usage, this does limit the potential application of the device.

According to the present invention there is provided a nozzle assembly for dispensing a unit dose of a substance, said nozzle assembly being intended for releasable attachment to a body having a system actuable to effect discharge of said substance, said nozzle assembly comprising a container housing a unit dose of said substance, means for releasably attaching the nozzle assembly to the body, and means co-operable with said discharge system whereby dispensing of the substance from the container is effected in response to actuation of the discharge system by the user.

Preferably, the discharge system comprises a ram and dispensing of the substance from the container occurs in response to movement of the ram.

Advantageously, the nozzle assembly comprises means for piercing the container in response to the movement of the ram.

Advantageously, the nozzle assembly includes a passage which receives the ram either when the nozzle assembly is being mounted on the body or subsequently thereto.

In a preferred embodiment of the invention, the container is in the form of a capsule mounted within a chamber in the nozzle assembly, and the piercing means comprises a first hollow needle mounted at an outer end of the chamber and a second hollow needle carried by a piston within an inner end portion of the chamber, with the capsule lying within the chamber between the first and second needles. The inner end portion of the chamber is in communication with the ram-receiving passage, the arrangement being such that the piston is displaceable within the chamber to displace the second needle towards the first needle to cause the two needles to pierce opposite ends of the capsule by movement of the ram along the passage. In this embodiment, the discharge system advantageously also includes means for injecting a gas, for example air, into the capsule via the second needle whereby the substance is dispensed from the capsule via the first needle under the effect of the gas injected via the second needle. The first needle may lead directly to an outlet orifice of the nozzle assembly or, as is preferred, the first needle may lead into a swirl chamber upstream of the outlet orifice. Preferably, the ram includes a passage through which air or other gas is injected into the capsule via the second needle.

In an especially advantageous embodiment, the means by which the nozzle assembly is attached to the body comprises a projecting tubular portion insertable into an opening in the body. The tubular portion includes a locking formation releasably engagable with locking means of the body adjacent the opening, and the tubular portion also includes the passage which receives the ram of the discharge system.

According to another aspect of the invention there is provided a body for use in cooperation with the nozzle assembly defined above, said body comprising a system to effect discharge of said substance from the nozzle assembly, means co-operable with the attachment means of the nozzle assembly to releasably retain the nozzle assembly relative to the body, and actuating means operable by a user to effect discharge.

In a preferred embodiment, the discharge system comprises a ram which is co-operable with the nozzle assembly to effect dispensing of the substance upon operation of the actuating means.

The body is preferably of a configuration such that it can be held in the hand of a user, and the actuating means of the body comprises at least one actuating member, such as a button, which can be actuated by a digit of the hand.

In one embodiment, displacement of the actuating member by the user is operative to cause displacement of the ram along the passage of the nozzle assembly. The displacement of the ram may be used to effect piercing of the container to enable the substance to be discharged. When dispensing is effected by injection of air into the container in the nozzle assembly, displacement of the actuating member is also effective to drive an air piston for charging air into the container. Preferably the air piston is spring-loaded and initial displacement of the actuating member serves to load the driving spring with spring energy which is subsequently released to drive the piston to inject air into the container. Preferably the system includes an air reservoir which communicates with an air passage through the ram and the air piston is operative to drive air from said air chamber through the air passage in the ram and into the container.

In another embodiment of the invention, mounting of the nozzle assembly to the body results in loading and cocking of a spring-driven air piston and displacement of the actuating member releases the piston to inject air into the container. The release of the piston also results in driving of the ram to effect piercing of the container.

Embodiments of the invention will now be described by way of example only with reference to the accompanying drawings in which:

FIG. 8 is a schematic side view of a second embodiment of a unit dose dispensing device in accordance with the invention and showing a main body of the device and a nozzle assembly for insertion into the main body;

FIG. 9 is a view similar to FIG. 8 but showing the nozzle assembly when inserted into the main body, and also a lid;

FIG. 10 is a schematic view showing the main body with the lid applied thereto to cover both the nozzle assembly and an actuating button;

Figure 17:
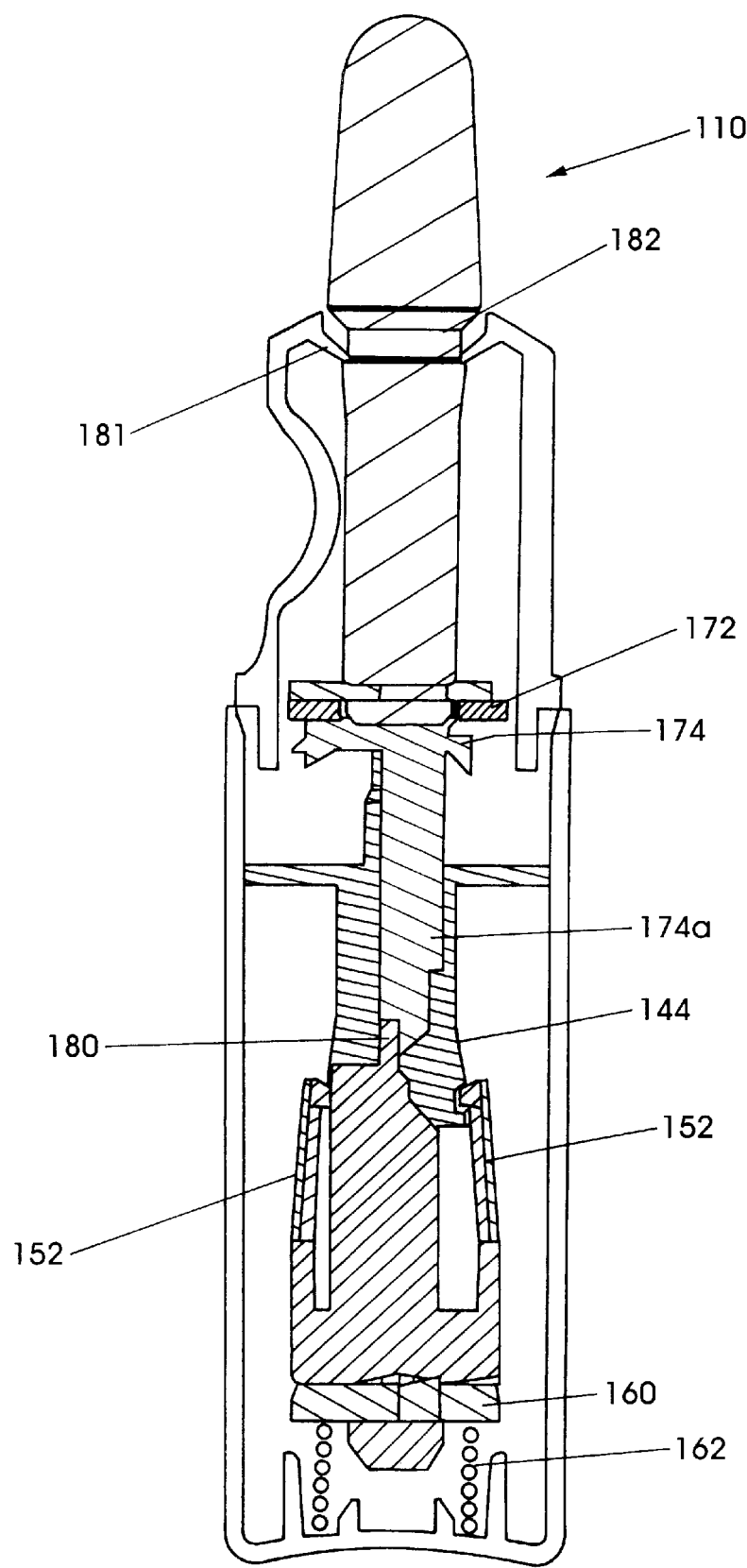
Figure 18:
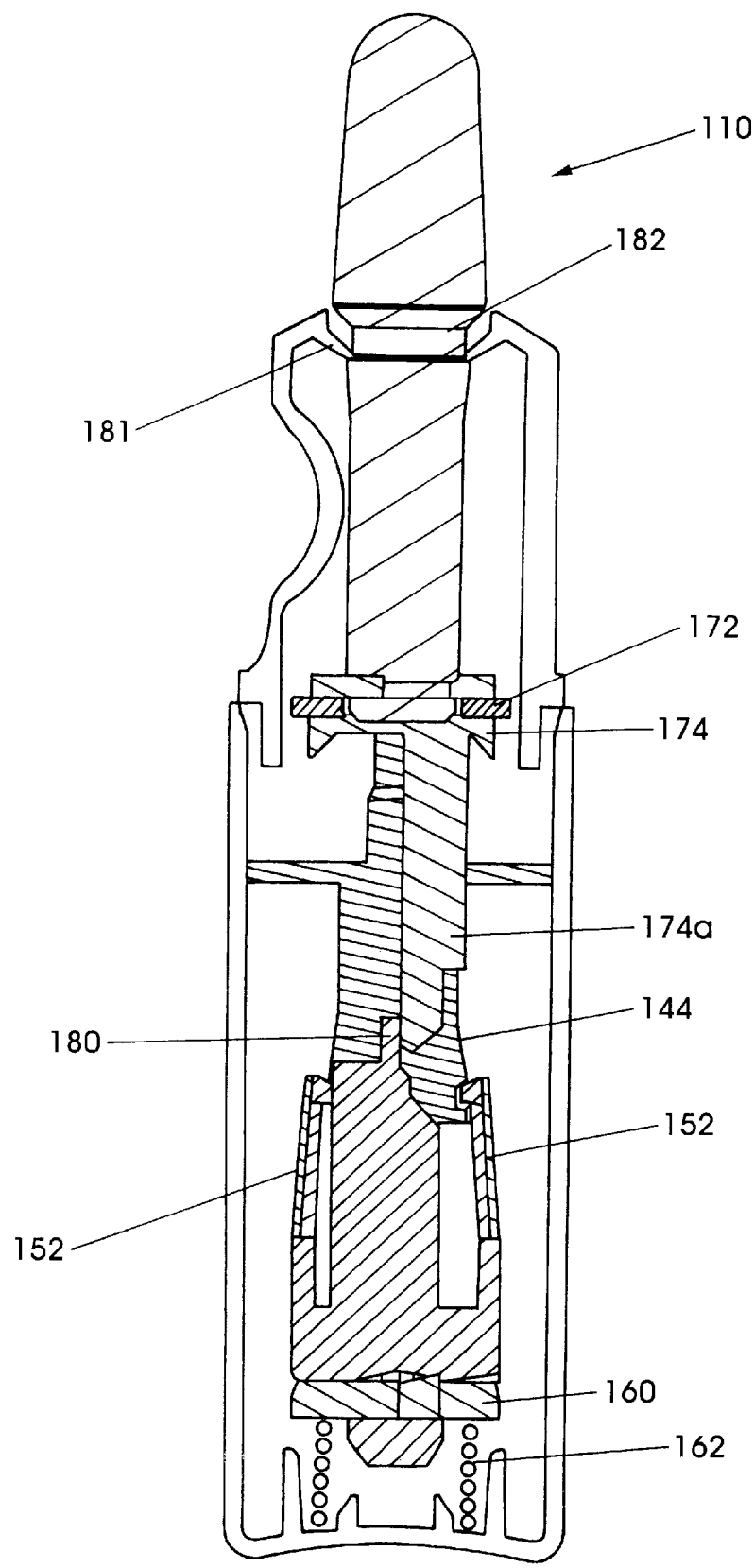
Figure 19:
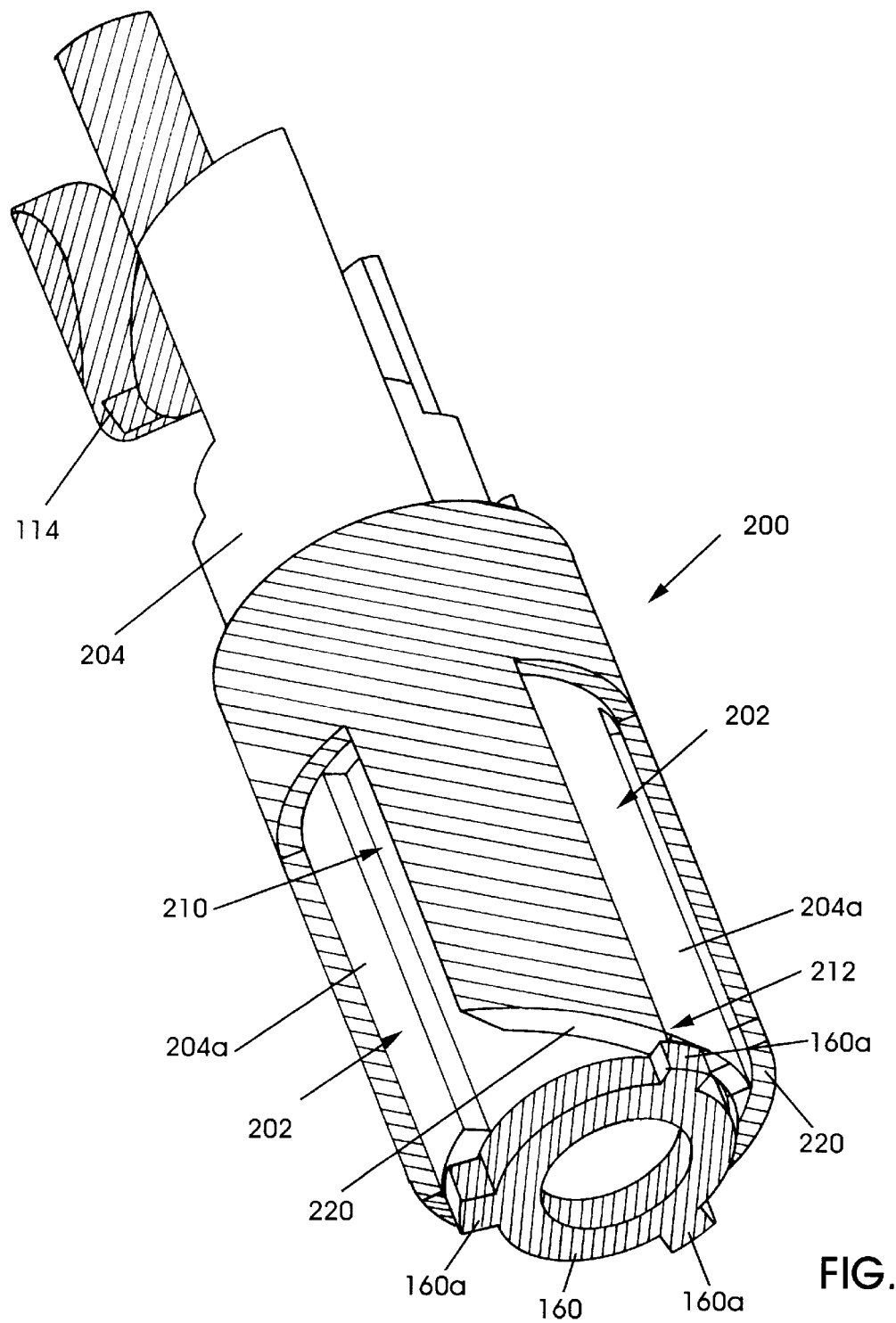
Figure 20:
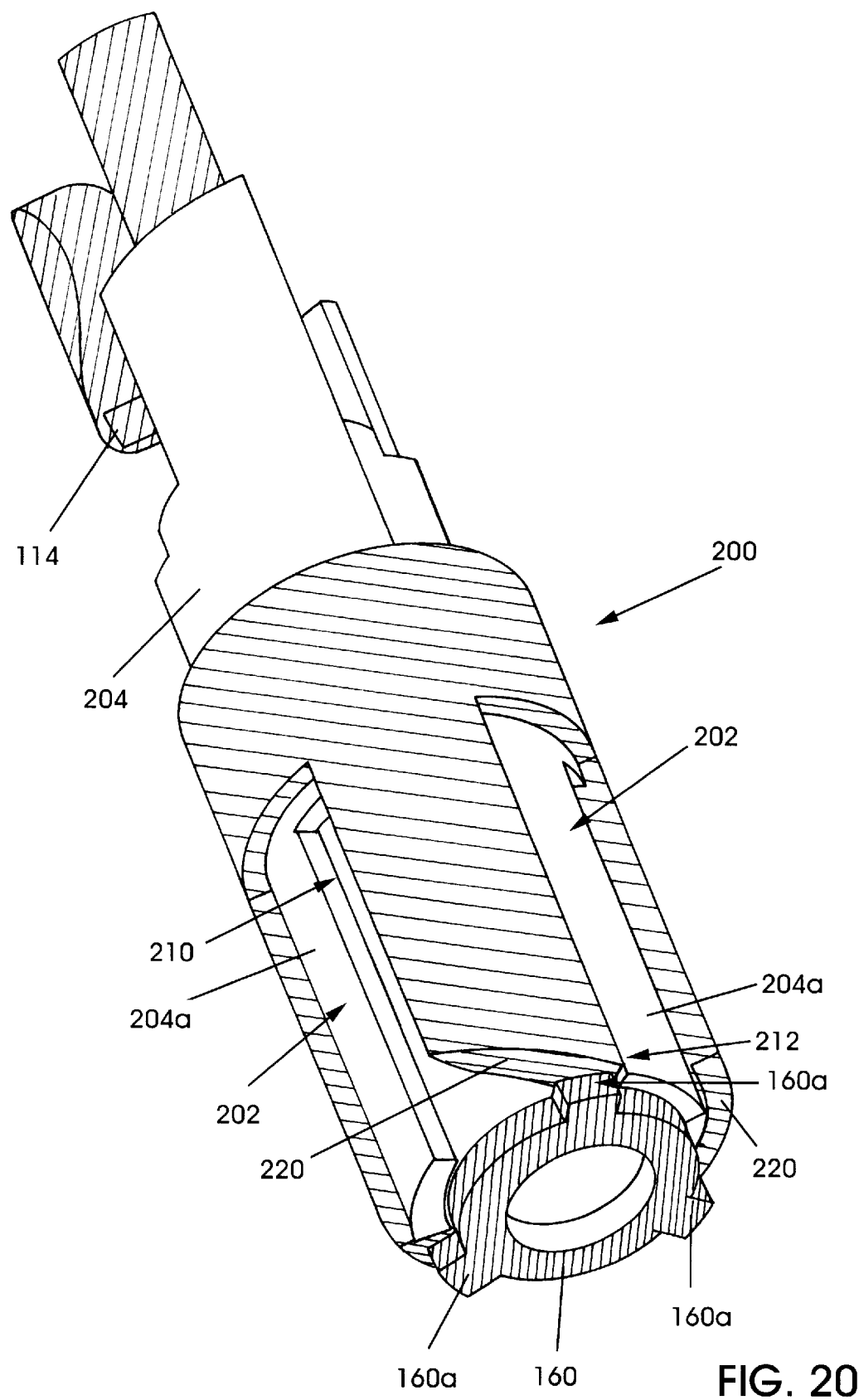
Figure 21:
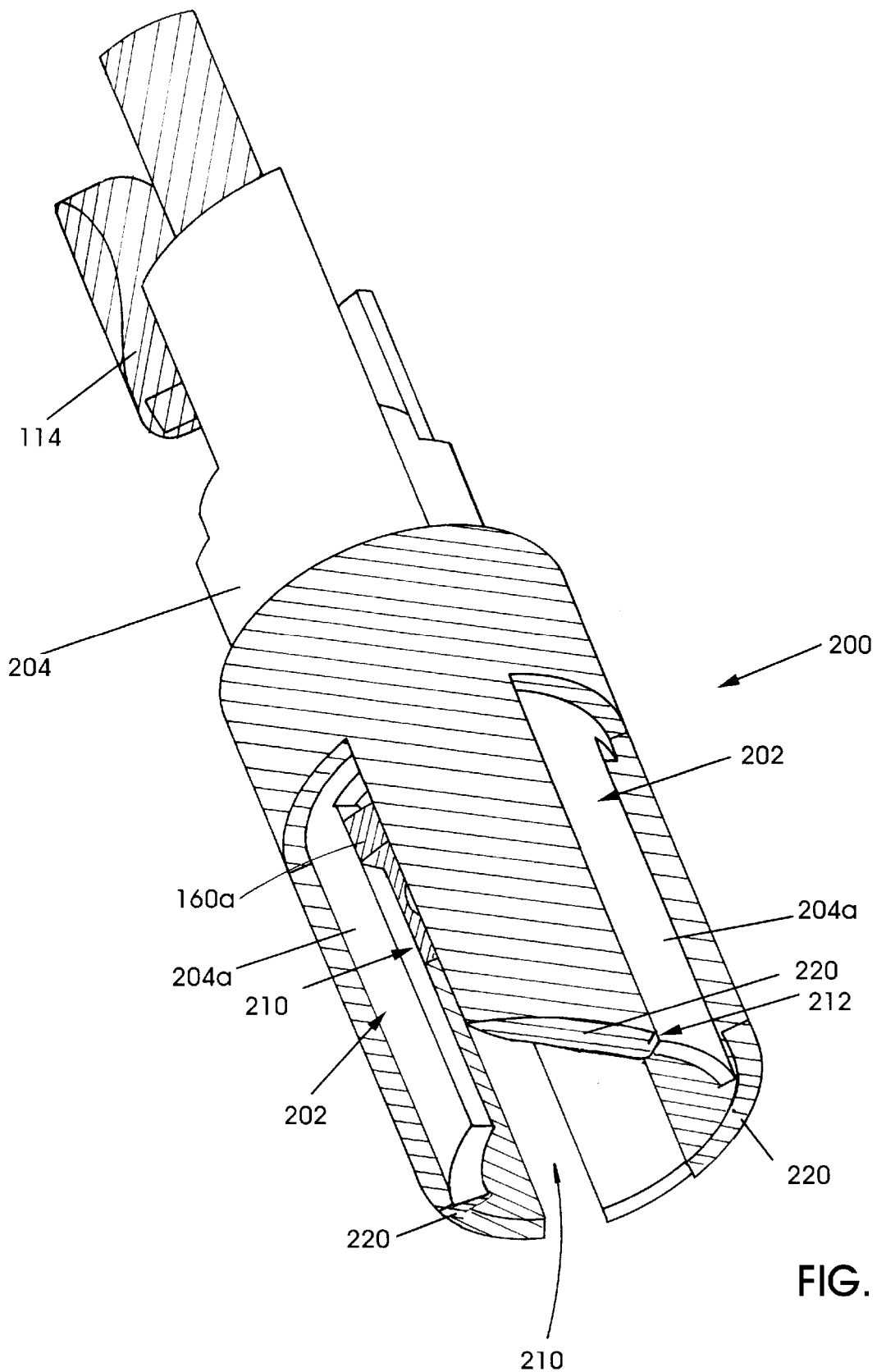

FIGS. 15 to 18 are simplified sections showing the cooperation between the nozzle assembly and the air piston/ cylinder assembly during various stages in the insertion and loading of the nozzle assembly into the device and which causes loading of the device; and FIGS. 19 to 21 are simplified schematic perspective views illustrating the cooperation between a register ring in contact with the piston of the air piston/cylinder assembly and a lock and firing ring, in different stages in the loading and firing of the device.

Figure 1:
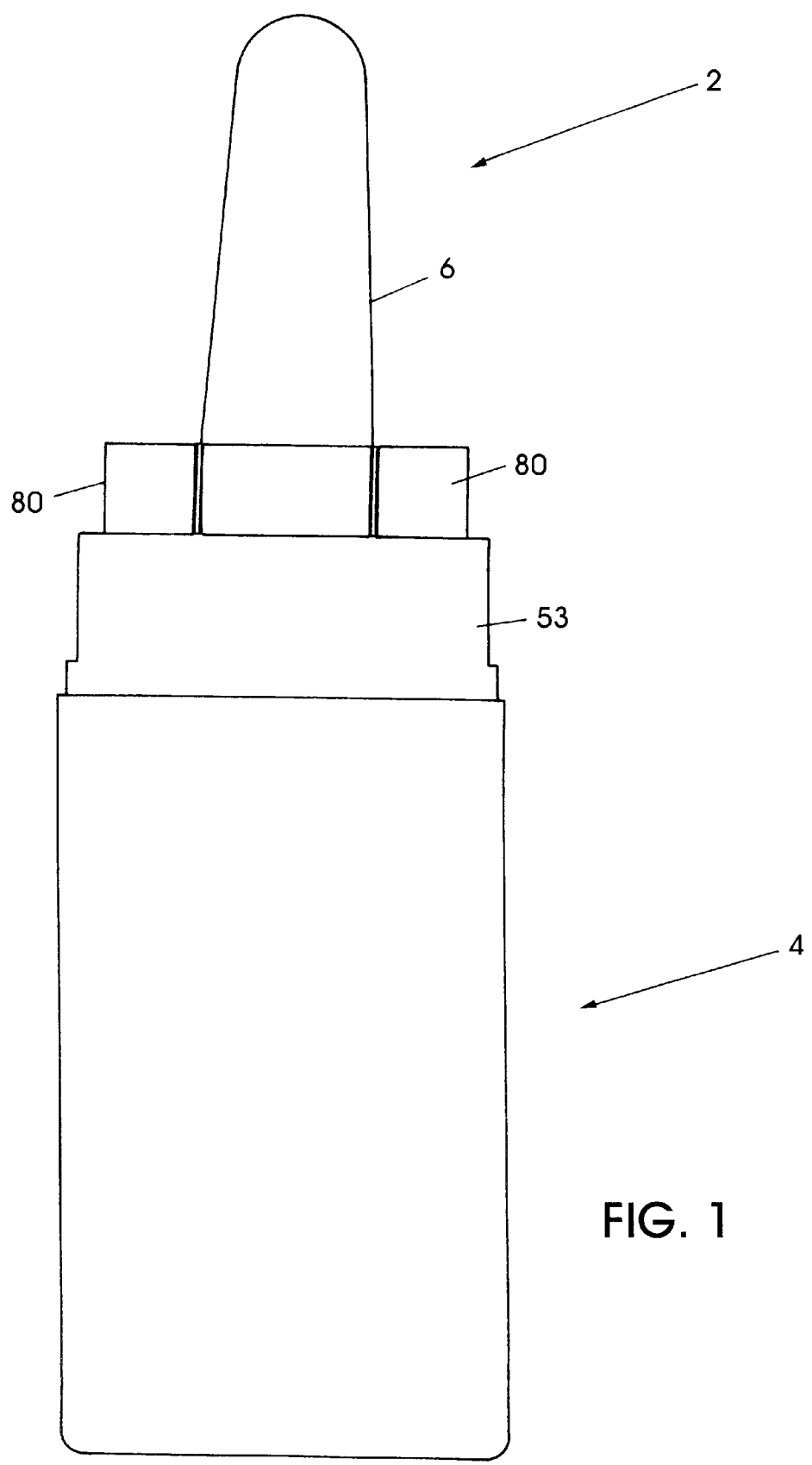
FIG. 1 is a schematic side view of a first embodiment of a unit dose dispensing device in accordance with the invention and comprising a nozzle assembly releasably attached to a main body of the device.

The unit dose dispensing device shown in FIG. 1 of the accompanying drawings comprises a nozzle assembly 2 carrying a unit dose of substance to be dispensed, the nozzle assembly 2 being releasably fitted into a main body 4 housing a mechanism which is actuated by the user to expel the unit dose. After usage, the spent nozzle assembly 2 is removed from the body 4, discarded, and replaced by a fresh nozzle assembly.

Figure 2:
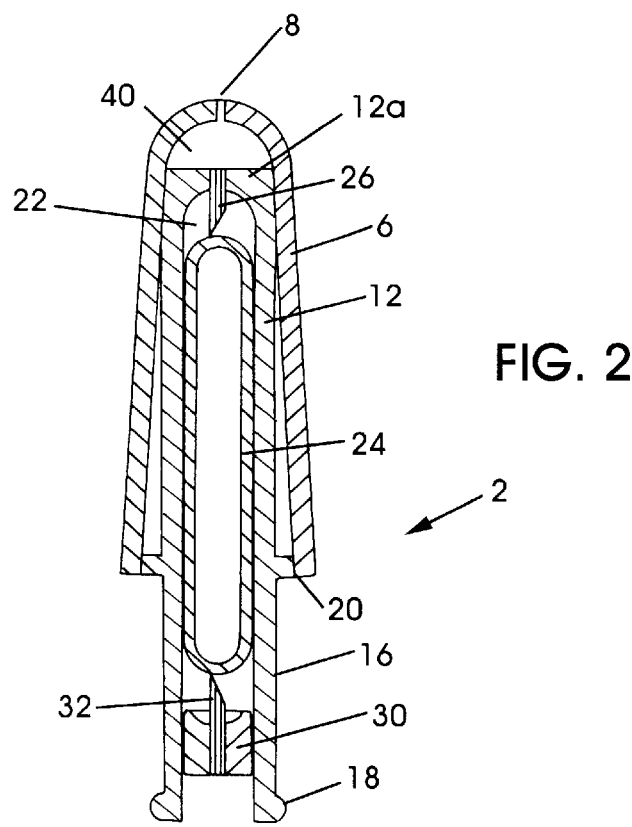
FIG. 2 is a section showing the nozzle assembly including a capsule of the unit dose of substance in a condition in which the nozzle assembly is able to be attached to the main body prior to discharge.

With particular reference to FIG. 2, the nozzle assembly 2 comprises an outer casing 6 with an outlet orifice 8 at its outer end . The nozzle assembly 2 illustrated is specifically intended for nasal administration of substance and accordingly the size of the outer casing 6 is appropriate for that usage. An inner sleeve 12 fixedly mounted within the outer casing 6 extends beyond the lower end of the outer casing 6 to form a fixing portion 16 which is inserted into the main body 4 of the device whereby to mount the nozzle assembly 2 to the main body 4 as will be subsequently described. The fixing portion 16 terminates in an external locking ring 18 which is intended to cooperate with locking fingers within the main body 4. An annular shoulder 20 at the lower end of the outer casing 6 is adapted to seat firmly against an annular support surface on the main body 4 when the nozzle assembly 2 is fi t ted onto the main body 4.

Figure 3:
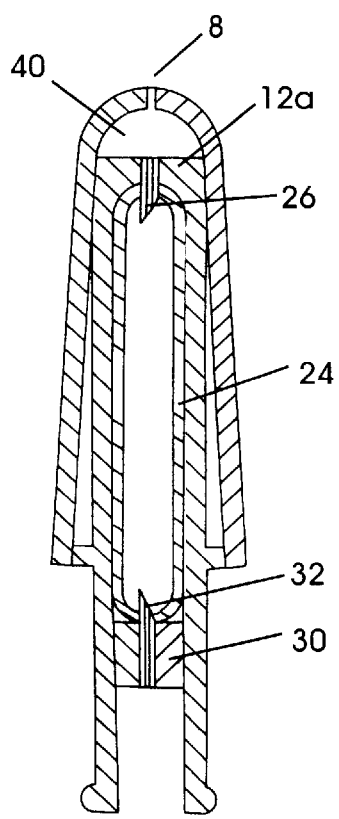
FIG. 3 is a section similar to FIG. 2 and showing the nozzle assembly in its condition after discharge of the unit dose and removal from the main body.

The inner sleeve 12 of the nozzle assembly 2 defines a chamber or cylinder 22 which houses a capsule 24 containing a unit dosage of the substance to be dispensed. The substance may be in liquid or powder form. An upper end wall 12a of the inner sleeve 12 carries a hollow needle 26 which projects into the upper end of the cylinder 22. The lower end portion of the cylinder 22 houses a piston 30 which carries a hollow needle 32. It will be seen from FIG. 2 that the capsule 24 is accordingly located within the cylinder 22 with the opposite ends of the capsule 24 adjacent the points of the upper and lower needles 26, 32. The nozzle assembly 2 is supplied to the user in this condition prior to usage. As will subsequently be described, when the nozzle assembly 2 is inserted into the main body 4 and the device is actuated by the user, the piston 30 carrying the lower needle 32 is driven along the cylinder 22 towards the upper needle 26. This action causes the capsule 24 to be pierced by both needles and to be pushed by means of the piston 30 so that its upper end sits firmly against the upper end wall 12a of the cylinder 22, with the upper needle 26 projecting into the interior of the capsule 24, and the face of the piston 30 seating firmly against the lower end of the capsule 24 with the lower needle 32 projecting into the lower end of the capsule; this condition is illustrated in FIG. 3. In this condition a substantial seal exists between the capsule 24 and the upper end wall 12a of the cylinder 22, and also between the face of the piston 30 and the lower end of the capsule 24, the piston 30 preferably being of a semi-soft material which ensures that a seal is formed. Air injected into the capsule 24 through the lower needle 32 as will be described causes the contents of the capsule 24 to be discharged through the upper needle 26. When the contents of the capsule 24 are in liquid form, the upper needle 26 preferably discharges into a swirl chamber 40 defined between the upper end wall 12a of the cylinder 22 and outer casing 6, the swirl chamber 40 discharging via the outlet orifice 8 in the outer casing 6. The swirl chamber 40 enhances droplet formation and facilitates discharge in spray form from the orifice 8.

As will be apparent, the capsule 24 is composed of a material which is able to be pierced by the needles 26, 32 and, preferably, is composed of a suitable plastics material. The capsule 24 may be formed by the blow fill seal moulding method which is well known per se.

Figure 4:
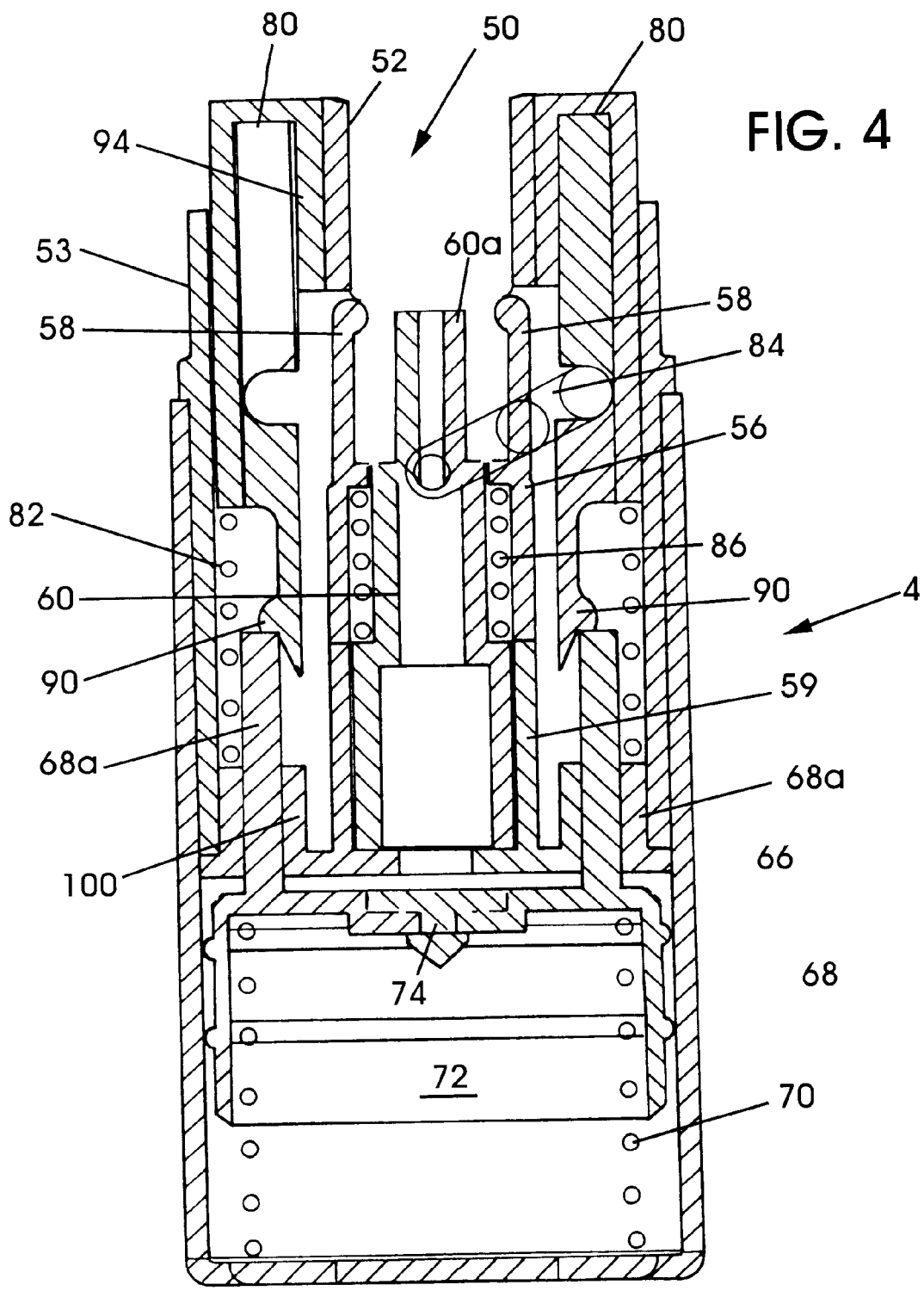
FIG. 4 is a cross-section showing the main body of the device in its condition prior to attachment of the nozzle assembly.
Figure 5:
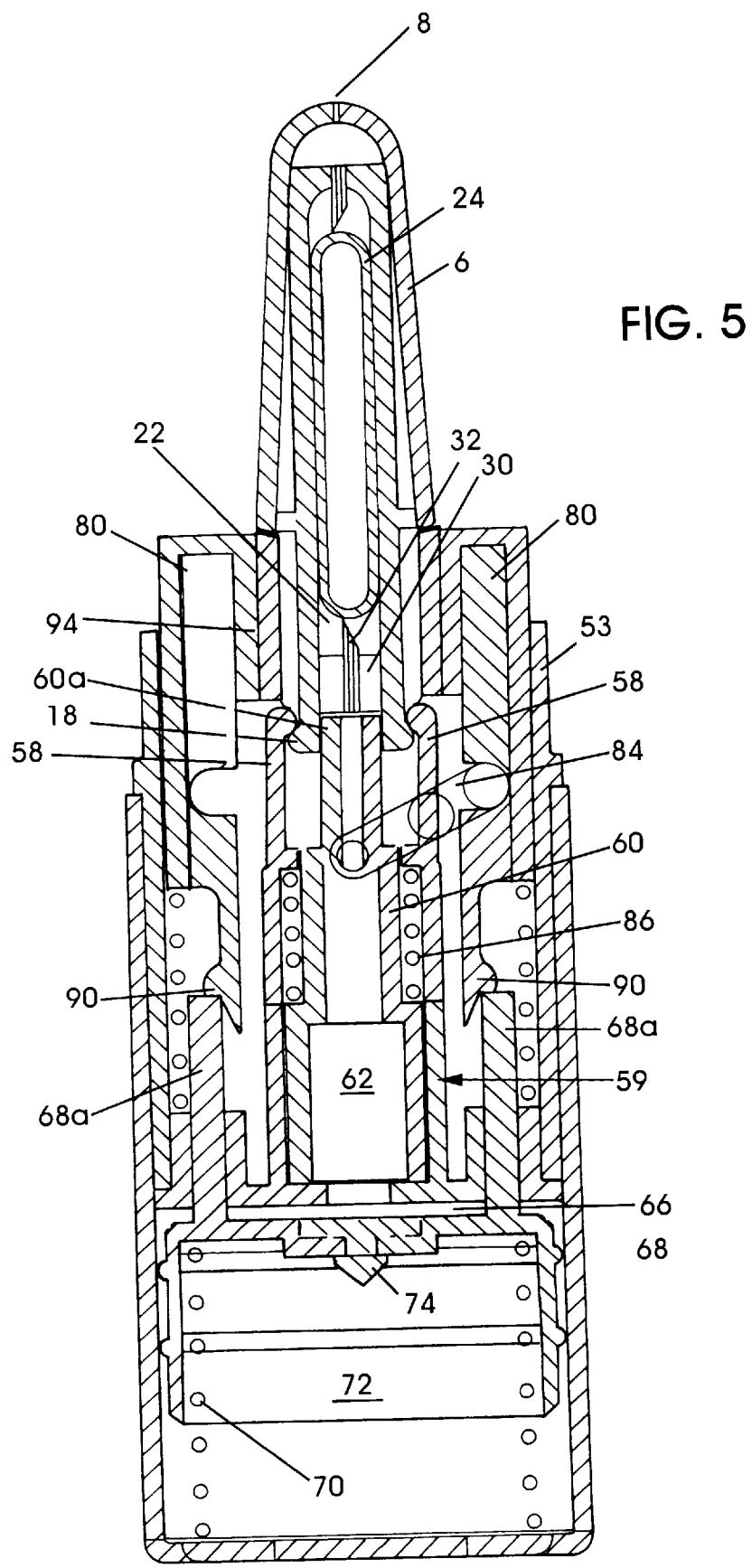
FIG. 5 is a cross-section of the device showing the condition when the nozzle assembly has been attached to the body and prior to actuation.

With reference to FIG. 4, the main body 4 of the device which contains the mechanism which is actuable to cause dispensing of the substance from the capsule 24, comprises a central passage 50 opening onto the upper end of the main body 4. The central passage 50 is intended to receive the fixing portion 16 at the lower end portion of the inner sleeve 12 of the nozzle assembly 2. The central passage 50 is defined by a fixed inner sleeve 52, the upper end edge of which defines the annular support surface engaged by the shoulder 20 on the nozzle assembly 2. The inner sleeve 52 forms an integral structure with an outer sleeve 53. A component 56 mounted in the main body 4 beneath the sleeve 52 carries opposed resilient fingers 58 which snap into engagement over the locking ring 18 on the fixing portion 16 to releasably lock the nozzle assembly 2 to the main body 4 (see FIG. 5). The component 56 is supported by a fixed structure 59 which also defines an axial guide for a ram 60, the upper end 60a of which engages into the lower end portion of the cylinder 22 so as to lie adjacent the lower end face of the piston 30 carrying the lower needle 32. The ram 60 also has an internal passage 62 which defines an air tube, the upper end of which communicates with the passage through the lower needle 32 and the lower end of which communicates with an air reservoir 66 defined between the fixed structure 59 and an air piston 68 mounted within the lower part of the main body 4. The air piston 68 is biased into an upper position adjacent the lower end of the fixed structure 59, and corresponding to a minimum volume of the air reservoir 66, by a compression spring 70. The air piston 68 is shown in this position in FIGS. 4 and 5. An air chamber 72 is defined between the air piston 68 and the base of the main body 4 and communicates with the air reservoir 66 via a one-way valve 74 in the crown of the air piston 68 whereby air is charged into the air reservoir 66 from the air chamber 72 via the one-way valve 74 upon movement of the air piston 68 towards the base of the main housing 4.

The main body 4 carries a button assembly comprising opposed buttons 80 at opposite sides of the fixed sleeve 52. The button assembly comprising the two buttons 80 is mounted for axial movement within the main body 4 between an outer position in which the outer ends of the two buttons 80 are substantially flush with the outer end of the fixed sleeve 52 (see FIGS. 4 and 5) and an inner position (see FIG. 7). The main body 4 is of a size such that it can readily be grasped in the hand of the user with the first finger and index finger engaging the respective buttons 80. It is to be noted that the two buttons 80 of the button assembly will move simultaneously even though they are adapted to be engaged by different fingers of the user. The button assembly is spring biased to its outer position by a compression spring 82 interposed between the button assembly and the fixed structure 59. The button assembly forms the means for actuating the device as will be now be described.

Figure 6:
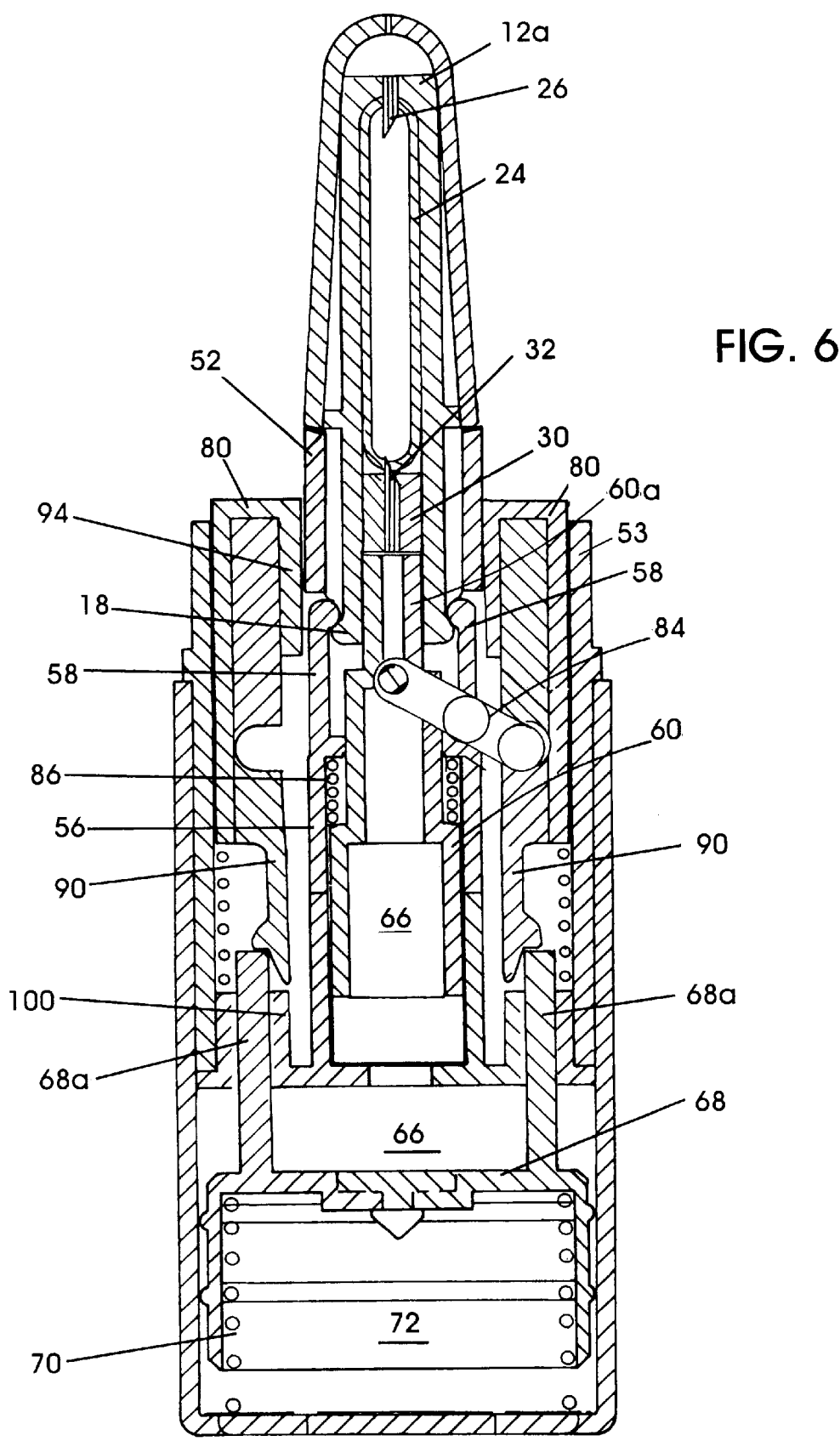
FIG. 6 is a section similar to FIG. 5 but showing the condition during actuation.

The button assembly is linked to the ram 60 by means of a lever 84 pivoted to the structure formed by the sleeves 52, 53 whereby pressing of the buttons 80 towards their inner position causes the lever 84 to drive the ram 60 upwardly against the bias of a compression spring 86. The upper end portion 60a of the ram 60 thereby displaces the piston 30 and lower needle 32 of the nozzle assembly upwardly to cause the upper and lower ends of the capsule 24 to be pierced by the two needles 26, 32 and also to drive the capsule 24 upwardly into engagement with the upper end wall 12a of the cylinder 22 as previously described. This condition is illustrated in FIG. 6. The button assembly also has depending resilient legs 90 which engage actuating stems 68a extending upwardly from the air piston 68 whereby depression of the buttons 80 also results in movement of the air piston 68 towards the base of the main body 4 against the bias of the compression spring 70 which is thereby loaded as the air piston 68 is displaced; this condition is likewise illustrated in FIG. 6. The displacement of the air piston 68 towards the ba se of the main body 4 causes air within the air chamber 72 to be discharged via the one-way valve 74 in the crown of the air piston 68 into the air reservoir 66 which increases in capacity as the air piston 68 is driven towards the base of the main body 4.

The button assembly is formed with an inner surface 94 which is coextensive with the fixed sleeve 52 when the button assembly is in its outer position. This is the normal "at rest" position of the button assembly and the nozzle assembly 2 is inserted into the main body 4 when the button assembly is in this state. When the button assembly is depressed, the inner surface 94 moves downwardly with the button assembly and passes along the outside of the resilient locking fingers 58 in order to prevent release of the fingers 58 from engagement with the locking ring 18 and hence release of the nozzle assembly 2 (again, see FIG. 6). Accordingly, while the resilient locking fingers 58 are able to releasably engage with the locking ring 18 of the nozzle assembly 2 with a snap action to perm it insertion of the nozzle assembly 2 prior to use and its removal after use, when the button assembly is depressed in the actuation of the device, the inner surface 94 of the button assembly acts as a locking surface which temporarily retains the locking fingers 58 so as to prevent release of the nozzle assembly 2 and hence to avoid the risk of accidental removal of the nozzle assembly 2 during actuation of the device.

Figure 7:
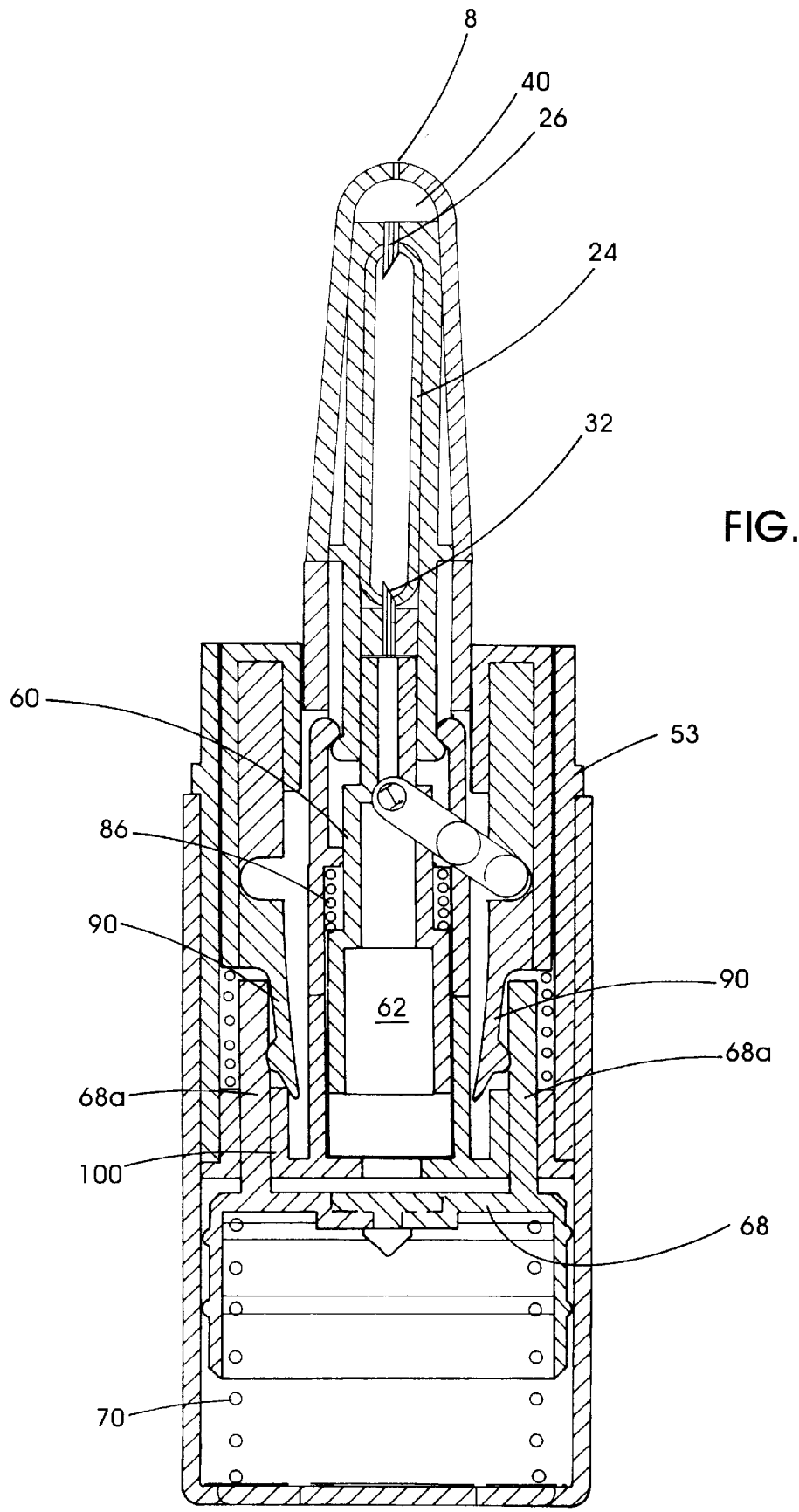
FIG. 7 is a section similar to FIG. 5 but showing the condition at the completion of actuation.

When the button assembly reaches the lower extent of its travel, the depending resilient legs 90 engage a cam cylinder 100 carried by the fixed structure 59, whereby the cam cylinder 100 deflects the legs 90 inwardly so as to release the legs from engagement with the stems 68a of the air piston 68. FIG. 6 illustrates the condition as the lower ends of the legs 90 approach the cam cylinder 100 shortly before release of the legs 90 from the piston stems 68a. With the air piston 68 thus released from restraint which occurs at the lower end of the displacement of the air piston 68, and with the compression spring 70 being at its maximum loading, the air piston 68 is then fired upwardly by the force in the compression spring 70 to discharge air from the air reservoir 66 via the air tube 62 and through the lower needle 32 into the capsule 24 to thereby cause discharge of the contents of the capsule 24 via upper needle 26, swirl chamber 40, and discharge orifice 8. This condition is illustrated in FIG. 7. Upon release of the buttons 80 of the button assembly, the button assembly will be returned to its outer position by the compression spring 82 to thereby release the locking restraint of the inner surface 94 on the locking fingers 58 and permit the nozzle assembly 2 to be removed and replaced by a fresh assembly for the next use; the ram 60 is also returned to its lower position (see FIG. 4) by the action of lever 84 and compression spring 86.

The device also includes a removable protective cap (not shown) which fits over the outer sleeve 53 to enclose the nozzle assembly 2 and the buttons 80. The cap prevents ingress of dirt into the mechanism and prevents accidental firing.

To enable a user readily to ascertain whether the nozzle assembly is a fresh assembly or has been used, preferably the fixing portion 16 of the nozzle assembly is transparent, and through which the piston 30 is visible. After use of the nozzle assembly the piston 30 will have been displaced upwardly as can be observed by the user.

It will be appreciated that in the embodiment just described, depression of the button assembly has the effect of piercing the capsule in preparation of release of the substance and also of "cocking" the air piston which is then triggered by release of the legs from the piston stems at the lower end of the travel of the button assembly and this results in discharge by the injection of air into the capsule.

In a second embodiment, cocking of the air piston can be effected by insertion of the nozzle assembly into the main body, with triggering to effect release of the cocked air piston being effected by actuation of a button assembly or other trigger. In this embodiment, the ram may be linked to the air piston so that the ram is not driven upwardly to cause piercing of the capsule until the device is triggered. Accordingly, in this embodiment the device can be stored in its loaded state for operation as soon as the trigger is actuated. This embodiment will now be described in detail with reference to FIGS. 8 to 21.

The unit dose dispensing device of the second embodiment comprises a nozzle assembly 110 carrying a unit dose of substance to be dispensed, the nozzle assembly 110 being releasably fitted into a main body 112 housing a mechanism which is actuated by the user to expel the unit dose. After usage the spent nozzle assembly is removed from the body 112, discarded, and replaced by a fresh nozzle assembly. As explained, insertion of the nozzle assembly into the main body 112 acts to cock the mechanism, the mechanism being released to expel the dose by actuation of a trigger in the form of a button 114. After insertion of the nozzle assembly 11 0, the device with the mechanism cocked in preparation for its next usage, can be conveniently stored by the user, for example in a pocket, purse, or handbag. In its storage mode a removable cap 116 is applied to the body 112 and encloses both the actuating button 114 and nozzle assembly 110.

Figure 11:
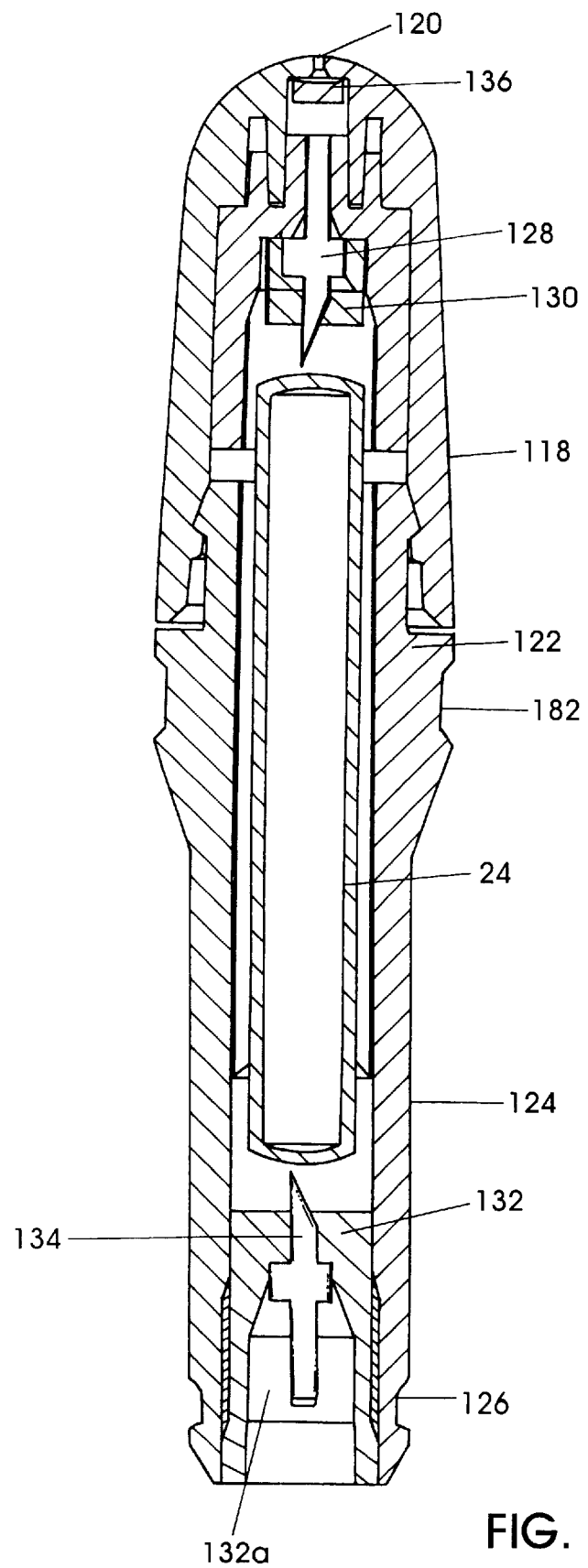
FIG. 11 is a section to a considerably enlarged scale showing the detailed structure of the nozzle assembly prior to insertion into the main body.

The nozzle assembly 110 is generally similar to the nozzle assembly of the preceding embodiment and is shown in detail in FIG. 11. The nozzle assembly 110 comprises an outer casing 118 with an outlet orifice 120 at its outer end. The nozzle assembly 110 illustrated is specifically intended for nasal administration of substance and accordingly the size of the outer casing 118 is appropriate for that usage. An inner sleeve 122 mounted within the outer casing 118 extends beyond the lower end of the outer casing 118 to form a fixing portion 124 which is inserted into the main body 112 of the device whereby to mount the nozzle assembly to the main body as will subsequently be described. The fixing portion 124 terminates in an external locking groove 126 which cooperates with a retainer system within the main body 112 as will subsequently be described.

The inner sleeve 122 of the nozzle assembly 110 defines a chamber or cylinder which houses the capsule 24 containing the unit dosage of the substance to be dispensed as described in connection with the previous embodiment. An upper end wall of the inner sleeve 122 carries a hollow needle 128 which projects into the upper end of the cylinder via a seal 130. The lower end portion of the cylinder houses a piston 132 which carries a hollow needle 134. The capsule 24 is therefore located within the cylinder with the opposite ends of the capsule 24 adjacent the points of the upper and lower needles 128, 134 and the nozzle assembly 110 is supplied to the user in this condition prior to usage (FIG. 11). The upper needle 128 communicates with the outlet orifice 120 via a swirl chamber 136 which enhances droplet formation as discussed in connection with the previous embodiment. The underside of the piston 132 is formed with a passage 132a which, when the nozzle assembly 110 is inserted into the main body 112, receives a ram 140 (see FIGS. 12 to 14) having an air passage 142 which communicates with an air cylinder 144 of an air cylinder/ piston assembly 146 of the mechanism within the main body 112. When the nozzle assembly 110 is inserted into the main body 112, the ram 140 locates within the passage 132a in the lower piston 132 and the lower needle 134 is in sealed communication with the air passage 142 in the ram 140 by engagement of the outer surface of the ram 140 in the passage 132a of the lower piston 132 as shown in FIGS. 12 to 14.

The ram 140 is integrally formed as an extension of the air cylinder 144 of the air cylinder/piston assembly 146. The air piston 148 of the air cylinder/piston assembly 146 is of tubular form carrying at its upper end a seal 150 which seals against the inner wall of the cylinder 144. The air piston 148 also includes a pair of opposed resilient arms 152 which can releasably lock into a locking groove 154 in the outer wall of the cylinder 144 to releasably retain the piston 148 at a lower end position within the air cylinder 144. The air piston 148 has at its lower end portion a register ring 160 which forms an important role in the cocking and firing of the mechanism as will subsequently be described. The register ring 160 is applied to the lower end of the air piston 148 so that the register ring 160 will move axially with the piston 148 but can rotate relative to the piston 148 about the axis of the piston. The air piston 148 is subject to an upwards spring bias provided by a compression spring 162 interposed between the register ring 160 and the lower end of the main body 112 of the device (see FIGS. 15 to 18).

Figure 12:
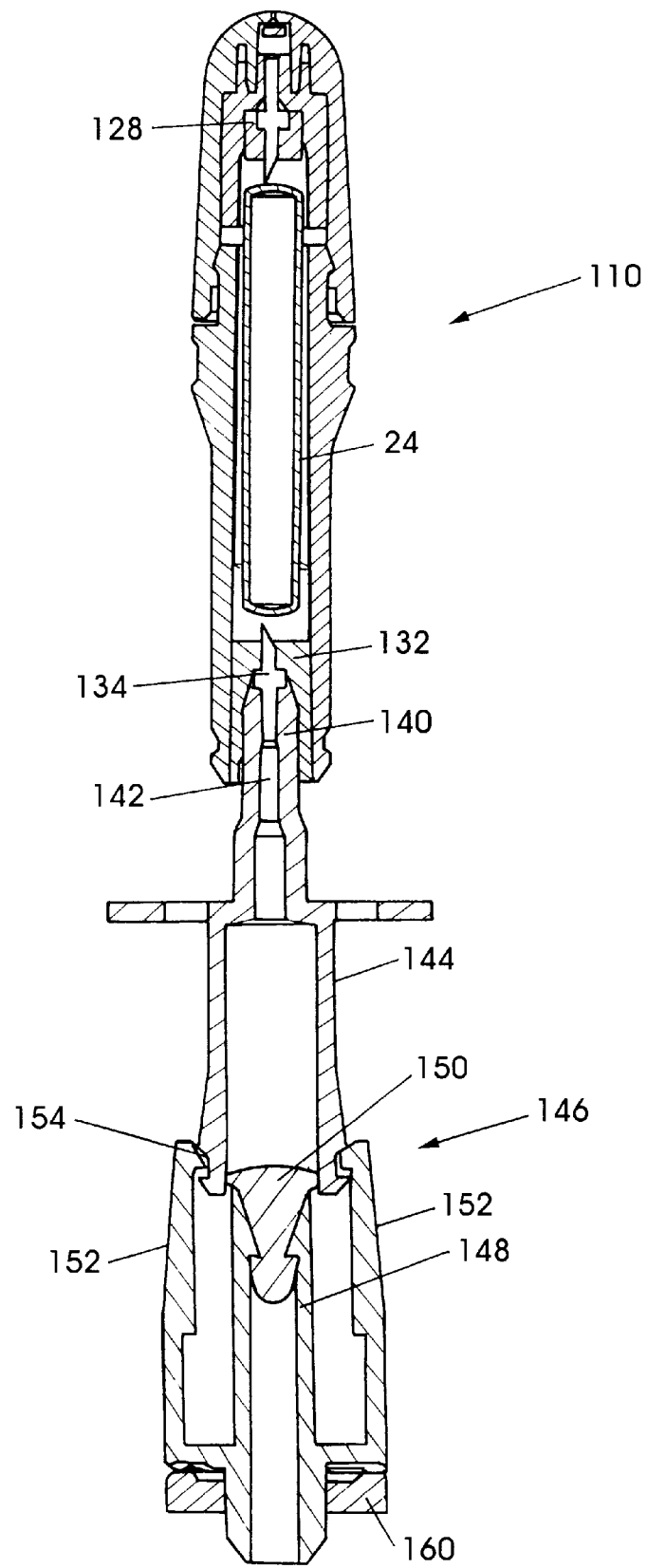
FIGS. 12 to 14 are simplified sections showing the nozzle assembly and its cooperation with an air cylinder/piston assembly during different stages during the firing of the device.
Figure 13:
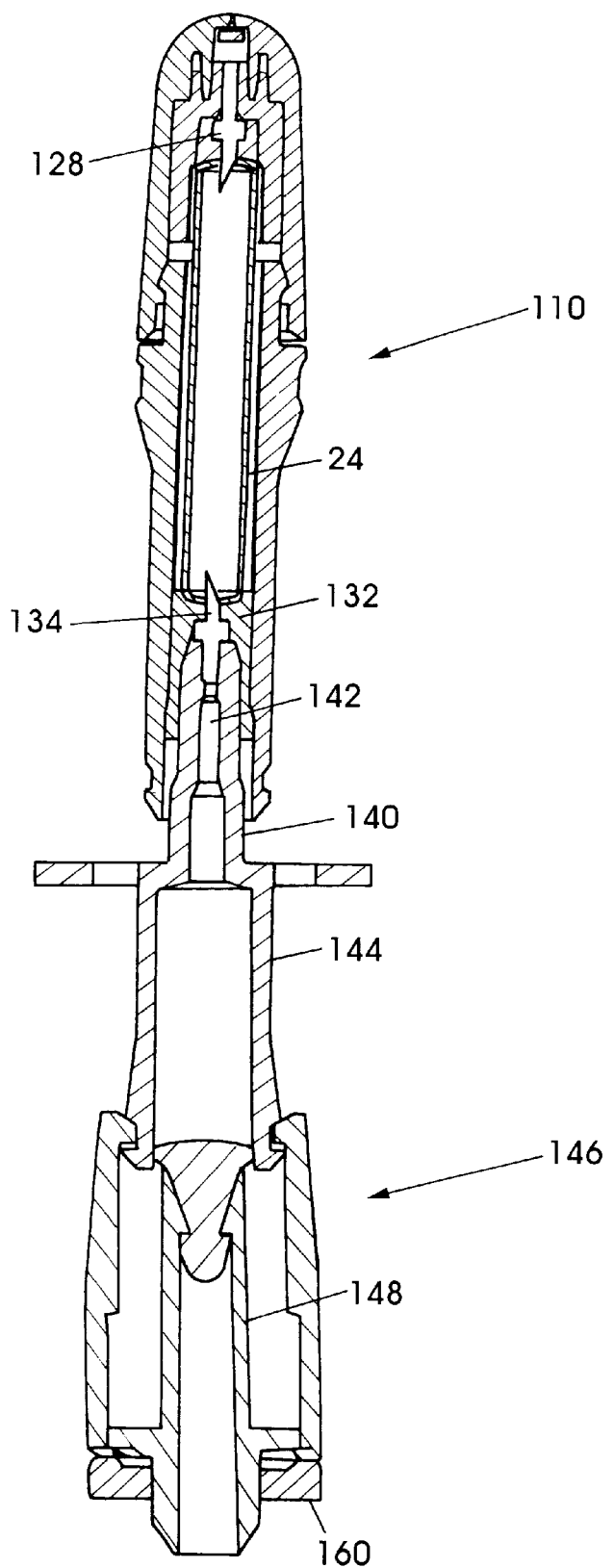
Figure 14:
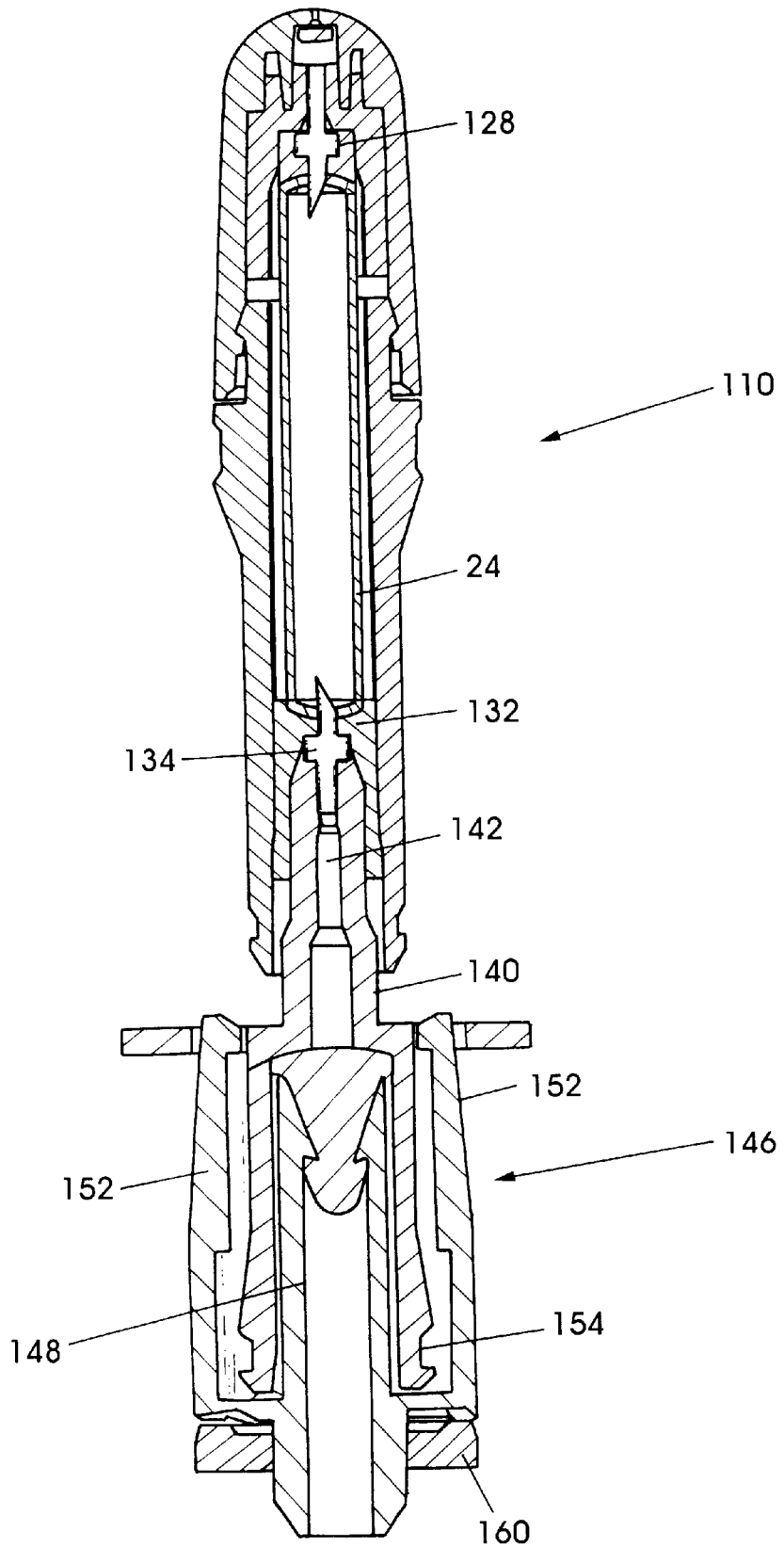

The basic sequence of operation or firing of the device is illustrated in FIGS. 12 to 14. FIG. 12 illustrates the configuration of the nozzle assembly 110 and air cylinder/piston assembly 146 after the nozzle assembly 110 has been inserted into the main body 112, whereby the mechanism is in a cocked state with the compression spring 162 acting on the register ring 160 and air piston 148 being in its loaded state. The manner in which the mechanism is held in the cocked state will be described in detail subsequently although a primary aspect of this arises from the cooperation between the register ring 160 and other components to be described. In this condition the ram 140 is seated within the lower piston 132 with the capsule 24 located between, but not yet pierced by, the upper and lower needles 128, 134. The air piston 148 is in a lowermost position relative to the air cylinder 144 and is releasably locked thereto by the locking fingers 152. When the actuating button 114 is depressed by the user, the register ring 160 is displaced to release the mechanism from its cocked state whereby the force of the compression spring 162 is released to drive the main air cylinder/piston assembly 146 upwardly as a unit whereby the ram 140 travels upwardly within the inner sleeve 122 of the nozzle assembly 110 to displace the lower piston 132 and capsule 24 upwardly to thereby cause the upper and lower needles 128, 134 to pierce the capsule 24 (see FIG. 13). Further upwards movement of the ram 140 and air cylinder 144 ceases as a result of the sealing engagement of the lower piston 132 against the lower end of the capsule 24, and under the continuing upwards loading of the compression spring 162 acting on the air piston 148 via the register ring 160, the releasable locking fingers 152 disengage from the locking groove 154 on the air cylinder 144 and the air piston 148 is driven upwardly along the air cylinder 144 whereby to force air via the air passage 142 of the ram 140 and lower needle 134 into the capsule 24 to thereby dispense the contents in the manner discussed in connection with the previous embodiment. FIG. 14 illustrates the configuration of the air cylinder/piston assembly 146 at the end of discharge or firing.

Figure 15:
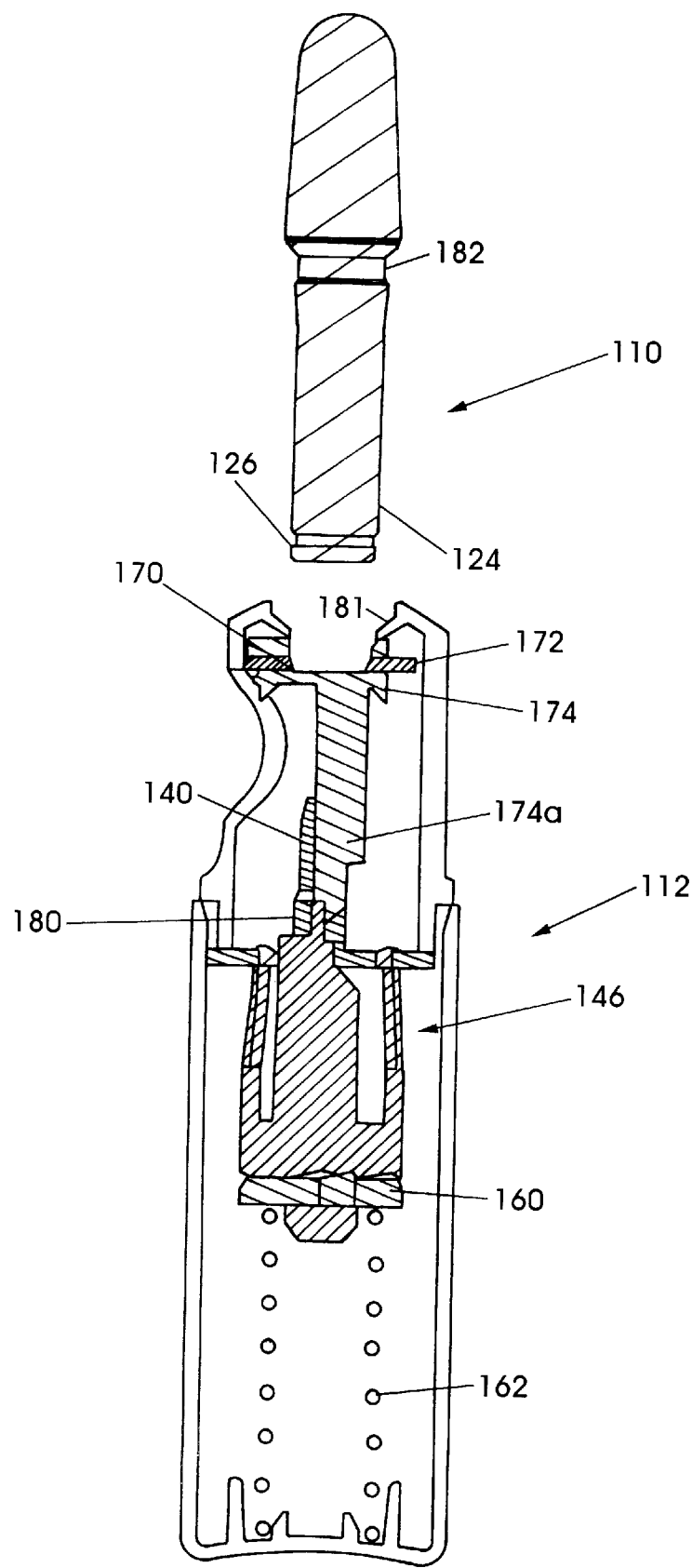
Figure 16:
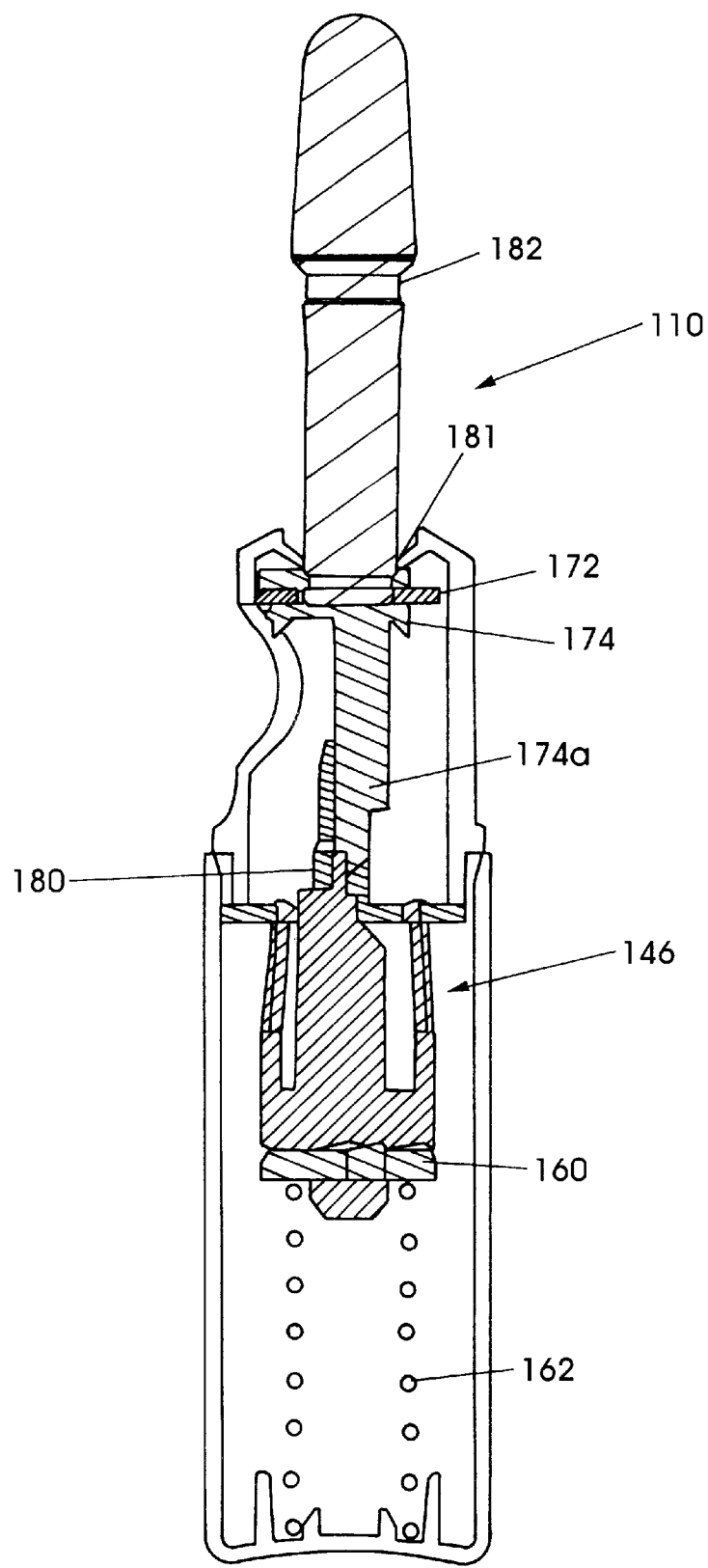

The manner in which a fresh nozzle assembly 110 is inserted and retained in the main body 112 resulting in loading and cocking of the mechanism will now be described with reference to FIGS. 15 to 18. FIGS. 15 and 16 illustrate the configuration after the end of discharge or firing of a previous nozzle assembly and subsequent removal of the previous nozzle assembly, with the air piston 148 at its uppermost position within the air cylinder 144. As shown in FIGS. 15 and 16, the lower end of the fixing portion 124 of the nozzle assembly 110 is locatable within a seat 170 in a shuttle 172 mounted for vertical movement within the upper end portion of the main body 112, the shuttle 172 constituting means for supporting the nozzle assembly 110 within the main body 112. The shuttle 172 is associated with a retainer 174 which acts to lock the nozzle assembly within the seat 170 and also performs other functions as will be described. The retainer 174 is mounted for vertical movement with the shuttle 172 but is also able to displace laterally relative to the shuttle 172 under the action of a relatively light spring bias provided by a spring (not shown). This lateral movement which occurs at the end of the insertion and cocking step causes locking ribs on the retainer 174 to engage within the peripheral locking groove 126 on the fixing portion 124 of the nozzle assembly 110 to thereby lock the fixing portion 124 in its seated position within the shuttle 172 (this is illustrated in FIG. 18). The retainer 174 in addition to its function of locking the nozzle assembly 110 to the shuttle 172 also acts to return the air piston 148 downwardly during insertion of the nozzle assembly 110 against the bias of the compression spring 162 thereby also loading the compression spring 162. For this purpose the retainer 174 has a depending portion shown at 174a which engages an abutment 180 on the structure of the air piston 148 externally of the cylinder 144. When the nozzle assembly 110 is inserted into the shuttle 172 at the upper end of the main body and is then pushed downwardly, the retainer 174 also moves downwardly with the shuttle and the depending portion 174a of the retainer 174 pushes the piston 148 downward against the bias of the compression spring 162 whereby the piston 148 is displaced downwardly along the air cylinder 144 to a lower position at which the locking fingers 152 re-engage within the groove 154 at the lower end of the air cylinder 144 (FIG. 17). Further downwards movement, typically by only a few millimetres, beyond the point at which the locking fingers 152 on the air piston 148 engage within the locking groove 154 in the air cylinder 144 results in the register ring 160 indexing into a locking position (as will be subsequently described) whereby the mechanism is held cocked against the force of the compressed compression spring 162. With the loading of the compression spring 162 now taken by the register ring 160 which maintains the mechanism in its cocked state, the retainer 174 is able to displace laterally relative to the shuttle 172 under the effect of the light lateral spring bias applied to the retainer 174, whereby to lock the nozzle assembly 110 within the shuttle 172 by engagement of the locking ribs in the locking groove 126 of the fixing portion 124 of the nozzle assembly 110. Also, this lateral movement of the retainer 174 causes the depending portion 174a of the retainer to be displaced laterally away from the abutment 180 of the air piston 148 so as to permit the air piston 148 subsequently to displace upwardly when the mechanism is fired by actuation of the button 114; in addition, the lateral displacement causes the retainer 174, and hence also the shuttle 172 and nozzle assembly 110 to lock against upwards displacement This is the configuration illustrated in FIG. 18.

FIGS. 15 to 18 also show a resilient locking lip 181 at the upper end of the main body. The locking lip 181 provides light support and location for the upper end of the nozzle assembly 110 during insertion, and in the inserted position of the nozzle assembly 110 the lip 181 engages within an annular groove 182 on the inner sleeve 122 of the nozzle assembly 110. The locking lip 181 also prevents accidental release of the nozzle assembly 110 during loading and before its fixing portion 124 has been locked within the seat 170 of the shuttle 172 by the lateral displacement of the retainer 174 at the end of the insertion stroke as described above.

As previously mentioned, the register ring 160 which is mounted at the lower end of the air piston 148 plays an important part in maintaining the mechanism in its cocked condition against the bias of the compression spring 162 and thereafter in permitting release or firing of the mechanism in order to expel the unit dose as described. The action of the register ring 160 will now be described with reference to FIGS. 19 to 21. Mounted within the main body 112 is a stationary lock 200 of generally cylindrical form. This is illustrated in FIGS. 19 to 21 but has been omitted from other Figures for the sake of clarity. The air cylinder/piston assembly 146 lies within the interior of the lock 200. The lock 200 has a plurality of axial slots 202 (as shown, three slots) extending upwardly from the bottom of the lock 200 and equi-angularly spaced around the axis of the lock 200. The register ring 160 which is also illustrated in FIGS. 19 to 21 has a corresponding number of radial lugs 160a also equi-angularly spaced around the axis of the ring 160. Also mounted within the interior of the lock 200 is a firing ring 204 of generally cylindrical form. The firing ring 204 interacts with the button 114 so that when the button 114 is depressed by the user, the firing ring 204 will be displaced downwardly within the lock 200. The firing ring 204 comprises a series of depending legs 204a each associated with one of the slots 202 in the lock 200. Each of the depending legs 204a of the firing ring 204 also defines with its associated slot 202 in the lock 200, an axial slot 210 into which a respective one of the radial lugs 160a on the register ring 160 can move when the register ring 160 is angularly indexed so that its radial lugs 160a are aligned with the respective slots 210.

FIG. 19 illustrates the configuration in which the nozzle assembly 110 has been inserted and the mechanism cocked (equivalent to FIGS. 12 and 18). In this condition each radial lug 160a is locked against upwards axial and rotational movement by engagement in a small step 212 defined between the end surface of the associated leg 204a of the firing ring 204 and a corner of the slot 202 in the lock 200. When the firing ring 204 is displaced downwardly by actuation of the button 114 the downwards displacement of the legs 204a of the firing ring 204 displaces the register ring 160 downwardly against the bias of the compression spring 162 so that the radial lugs 160a move out of the locking steps 212. When so released, inclined co-operating cam surfaces defined by the upper surfaces of the radial lugs 160a and the end surfaces of the associated legs 204a of the firing ring 204 induce, under the effect of the compression spring bias acting on the register ring 160, a slight rotation of the register ring 160 so that the upper surface of each radial lug 160a moves onto an inclined cam surface 220 formed at the lower end of the lock 200 between the adjacent slots 202. As a result of the axial bias applied by the compression spring 162, the radial lugs 160a are caused to move along the cam surfaces 220 with both axial and rotational displacement (see FIG. 20) until the lugs 160a reach the next adjacent axial slot 210 defined between the slot 202 in the lower lock and the leg 204a in the firing ring 204 and when entering that slot, the register ring 160 can then displace axially to the upper end of the slot 210 to thereby engender the displacement of the air cylinder piston assembly 146 and then of the air piston 148 to effect the piercing of the capsule and discharge of the contents as previously described. This mode is illustrated in FIG. 21.

FIG. 21 illustrates the configuration at the end of the firing action and, essentially, this is the same configuration that exists after removal of the nozzle assembly 110 following discharge. When a new nozzle assembly 110 is being inserted as previously described with reference to FIGS. 15 to 18, the downwards displacement of the air piston 148 as a result of the interaction between the retainer 174 and piston 148 during insertion results in downwards movement of the register ring 160. When the radial lugs 160a of the register ring 160 have moved downwardly along the slots 210 and beyond the slots 210 to a sufficient extent to clear the lower end edge of the adjacent leg 204a of the firing ring 204, a camming action between the register ring 160 and air piston 148 under the effect of the axial bias applied by the now compressed compression spring 162 will engender a rotation of the register ring 160 so that the lugs 160a are angularly displaced away from the slots 210 and onto the end surfaces of the legs 204a where they will be held in the locking steps 212 against further axial and rotational displacement until the next actuation of the firing ring 204 by depressing the button 114. This, again, is the configuration illustrated in FIG. 19 and it will be appreciated that through the sequence of actions thus described, the register ring 160 during the firing and subsequent cocking action has undergone a series of axial and rotational movements whereby it has indexed through a step of 120° within each complete operational cycle. It is to be noted that the camming action between the register ring 160 and air piston 148 as just described is provided by inclined cooperating cam surfaces on the upper surface of the register ring 160 and under surface of the air piston 148.

It will be recalled that during the act of insertion of the nozzle assembly 110, the shuttle 172 and retainer 174 are displaced downwardly by the nozzle assembly 110, resulting in the downwards displacement of the air piston 148. During this action the retainer 174 moves downwardly along a vertical guide groove within the main body 112. At the end of the insertion action which results in the lateral displacement of the retainer 174 (FIG. 18) whereby to lock the nozzle assembly 110 within the shuttle 172, the retainer 174 moves out of the vertical guide groove whereby the retainer 174, shuttle 172, and nozzle assembly 110 are locked within the main body 112 against upwards axial displacement. At the end of the firing action, slight depressing of the nozzle assembly 110 by the user will result in further lateral displacement of the retainer 174 under the lateral spring bias to which it is subjected whereby the retainer 174 enters a further vertical guide groove and the retainer 174, shuttle 172, and nozzle assembly 110 can then be drawn upwardly. Towards the end of that upwards movement when the shuttle 172 is adjacent the upper end of the main body 112, the groove within which the retainer 174 is mounted causes lateral displacement of the retainer 174 in the opposite direction whereby to permit release of the nozzle assembly 110 from locking engagement with the shuttle 172 and the nozzle assembly can thereby be withdrawn. After removal of the nozzle assembly 110, a second lateral spring acting on the retainer 174 ensures that the retainer 174 is displaced laterally so that it is returned to a position in which the shuttle 172 can accept a new nozzle assembly 110.

The device of the second embodiment can be of an overall size similar to that of a container for lipstick and can conveniently be carried by the user, for example in a pocket, a purse or a handbag.

The devices described are suited for intranasal administration of the drug sumatriptan for use, for example in the treatment of migraine. It is however to be understood that the devices can also be used for the intranasal administration of other substances such as fluticasone propionate and beclomethasone dipropionate for the treatment of respiratory disorders such as allergic rhinitis. The devices can also be used for oral administration of substances or for administration of substances into other body cavities and also into the lung.

Although in the devices particularly described the nozzle assembly comprises a capsule which is pierced at opposite ends by hollow needles and discharge is effected by injecting air into the capsule in an alternative form the substance to be dispensed may be contained within a cylinder within the nozzle assembly, with the body of the cylinder or a piston within the cylinder being displaced by actuation of the ran to cause discharge of the contents by the effect of displacement and without injecting air. However the use of the capsule with air injection for discharge is preferred as it provides an effective means of ensuring discharge of the required unit dose in spray form and without requiring excessive actuating forces to be applied by the user. Also the capsules themselves can be manufactured inexpensively with existing equipment.

In the devices described herein, most of the components can be moulded from suitable plastics materials. The nozzle assembly containing the substance to be dispensed is a single-use "consumable" item. The nozzle assembly is of relatively simple construction and can be produced relatively inexpensively. The main body of the device which contains the major components of the dispensing mechanism is, of course, retained for repeated re-use with fresh nozzle assemblies. Although the components of the main body will need to be of a relatively robust construction in order to operate over many cycles of use, nevertheless the relative cost of the main body can be tolerated as it is not a single-use item. Attachment and removal of the nozzle assembly is very simple and the forces required to be exerted by the user to actuate the device are relatively low and are well within the physical capabilities of the likely range of users, including the e elderly or physically disabled.

The embodiments have been described by way of example only and modifications are possible within the scope of the invention.

What is claimed is:

1. A nozzle assembly for intranasal administration of a unit dose of a substance, said nozzle assembly being adapted for releasable attachment to a body having a system actuable to effect discharge of a substance, said nozzle assembly comprising a container which houses a unit dose of a substance, means for releasably attaching the nozzle assembly to the body, and dispensing means co-operable with said discharge system whereby the discharge system of the body comprises a ram, and the dispensing means of the nozzle assembly comprises means for piercing the container in response to the movement of the ram, such that dispensing of a substance from the container occurs in response to movement of the ram.

2. A nozzle assembly according to claim 1, wherein the nozzle assembly includes a passage which receives the ram either when the nozzle assembly is being mounted on the body or subsequently thereto.

3. A nozzle assembly according to claim 1, wherein the container is in the form of a capsule mounted within a chamber in the nozzle assembly, and the piercing means comprises a hollow needle mounted at an outer end of the chamber whereby the capsule is displaceable by the action of the ram towards the outer end of the chamber to cause piercing by the needle.

4. A nozzle assembly according to claim 1, wherein the discharge system of the body comprises means for injecting gas into the container, and wherein the container within the nozzle assembly is in the form of a capsule mounted within a chamber in the nozzle assembly, and the piercing means comprises a first hollow needle mounted at an outer end of the chamber and a second hollow needle carried by a piston within an inner end portion of the chamber, with the capsule lying within the chamber between the first and second needles, the arrangement being such that the piston is displaceable within the chamber under the action of the ram to displace the second needle towards the first needle to cause the two needles to pierce opposite ends of the capsule, whereby dispensing gas from the discharge system of the body can be injected into the capsule via the second needle such that a substance is dispensed from the capsule via the first needle under the effect of the injected gas.

5. A nozzle assembly according to claim 4, wherein the first needle leads into a swirl chamber upstream of an outlet orifice of the nozzle assembly.

6. A body for use with a nozzle assembly according to claim 4, said body comprising a system to effect discharge of a substance from the nozzle assembly, means co-operable with the attachment means of the nozzle assembly to releasably retain the nozzle assembly relative to the body, and actuating means operable by a user to effect discharge, wherein the discharge system comprises a ram which is co-operable with the nozzle assembly to effect piercing of the capsule by the first and second needles, said discharge system further comprising means for injecting air into the capsule via the second needle whereby to cause discharge of a substance via the first needle.

7. A body according to claim 6, wherein the ram includes an air passage which communicates with the second needle for injection of air into the capsule.

8. A body according to claim 7, wherein the means for injecting air comprises an air piston which is spring-loaded to inject air into the capsule via the air passage in the ram upon operation of the actuating means by the user.

9. A body according to claim 8, wherein the actuating means is operative initially to load a driving spring of the air piston with spring energy and to thereafter release said spring energy whereby the air piston is driven to inject air.

10. A body according to claim 8, wherein the means for releasably retaining the nozzle assembly comprises support means for the nozzle assembly, said support means being displaceable by the nozzle assembly when mounting the nozzle assembly to the body, said movement of the support means serving to load a driving spring of the air piston with spring energy, and means for retaining the driving spring in its loaded state, said retaining means being releasable in response to operation of the actuating means by the user whereby the air piston is then driven by the driving spring to effect discharge of a substance.

11. A body according to claim 10, for use with a nozzle assembly according to claim 6, wherein the support means is adapted to cooperate with the inner end of the protecting tubular portion of the nozzle when the tubular portion is inserted into the body, and the support means is displaceable within the body as a result of insertion movement of the tubular portion of the nozzle assembly in the direction of the axis of the tubular portion.

12. A body according to claim 11, wherein the means for releasably retaining the nozzle assembly further comprises means for releasably locking the tubular portion of the nozzle assembly to the support means to prevent release of the nozzle assembly during discharge.

13. A body according to claim 8, wherein the actuating means is linked to the ram such that initial operation of the actuating means displaces the ram to cause piercing of the capsule prior to release of spring energy of a driving spring of the air piston.

14. A body according to claim 8, wherein the ram is subject to the action of a driving spring of the air piston such that release of a spring energy upon operation of the actuating means will also effect driving movement of the ram to effect piercing of the capsule.

15. A nozzle assembly according to claim 1, wherein the means for releasably attaching the nozzle assembly to the body comprises a projecting tubular portion of the nozzle assembly insertable into an opening in the body, the tubular portion including a locking formation releasably engagable with locking means of the body.

16. A nozzle assembly according to claim 15 when dependent on claim 2, wherein the tubular portion includes the passage which receives the ram of the discharge system.

17. A nozzle assembly according to claim 1, wherein the outer end portion of the nozzle assembly is of a size such that it can be inserted into a nasal cavity.

18. A body for use with a nozzle assembly according to claim 1, said body comprising a system to effect discharge of a substance from the nozzle assembly, means co-operable with the attachment means of the nozzle assembly to releasably retain the nozzle assembly relative to the body, a and actuating means operable by a user to effect discharge wherein the discharge system comprises a ram which is co-operable-with the nozzle assembly.

19. A body according to claim 18, wherein the body is of a configuration such that it can be held in a hand of a user and the actuating means comprises at least one actuating member which can be actuated by a digit of the same hand.

20. A nozzle assembly for dispensing a unit dose of a substance, said nozzle assembly being adapted for releasable attachment to a body having a system actuable to effect discharge of a substance by the injection of air, said nozzle assembly comprising a capsule housing a unit dose of a substance, said capsule being mounted between outer and inner hallow needles at opposite ends of the capsule, the inner needle being displaceable towards the outer needle under the action of a ram so as to pierce the capsule whereby dispensing of a substance can then be effected by injecting air from the discharge system of the body into the capsule via the inner needle with a substance being discharged from the capsule via the outer needle.

21. A device for dispensing a unit dose of a substance comprising a nozzle assembly for intranasal administration of a unit dose of a substance, said nozzle assembly being adapted for releasable attachment to a body having a system actuable to effect discharge of a substance, said nozzle assembly comprising a container which houses a unit dose of a substance, means for releasably attaching the nozzle assembly to the body, and dispensing means co-operable with said discharge system whereby the discharge system of the body comprises a ram, and the dispensing means of the nozzle assembly comprises means for piercing the container in response to the movement of the ram, such that dispensing of a substance from the container occurs in response to movement of the ram, and a body according to claim 18, the nozzle assembly being attachable to the body for cooperation with the discharge system of the body.

22. A device for dispensing a unit dose of a substance, said device comprising a nozzle assembly including a container housing a unit dose of a substance, and a body to which the nozzle assembly is releasably attached, said body including a system actuably to effect discharge of a substance from the nozzle assembly, and actuating means operable by a user to effect discharge, the nozzle assembly being removable from the body after use and being replaceable by a further such nozzle assembly to permit dispensing of a unit dose of a substance from that nozzle assembly, wherein the discharge system comprises a spring-loaded air piston actuable to inject air into the container to cause discharge of a substance.

23. A device according to claim 22, wherein a driving spring for the air piston is loaded with spring energy by the action of installing the nozzle assembly on the body, said driving spring thereafter being held in a cocked state until operation of the actuating means by the user to effect release of the spring energy to cause discharge.

* * * * *